(12) United States Patent
Wu et al.

(10) Patent No.: US 7,708,698 B2
(45) Date of Patent: May 4, 2010

(54) CIRCUIT FOR MEASURING BREATH WAVEFORM WITH IMPEDANCE METHOD AND METHOD AND DEVICE FOR RESISTING INTERFERENCE OF ELECTRICAL FAST TRANSIENT

(75) Inventors: Xiaoyu Wu, Shenzhen (CN); Yu Sun, Shenzhen (CN); Jian Cen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1168 days.

(21) Appl. No.: 11/316,454

(22) Filed: Dec. 21, 2005

(65) Prior Publication Data

US 2007/0004988 A1 Jan. 4, 2007

(30) Foreign Application Priority Data

Jun. 29, 2005 (CN) .................. 2005 1 0035608

(51) Int. Cl.
*A61B 5/08* (2006.01)
(52) U.S. Cl. ....................... 600/536; 600/529
(58) Field of Classification Search ............ 600/536
See application file for complete search history.

(56) References Cited

U.S. PATENT DOCUMENTS

| | | | | |
|---|---|---|---|---|
| 4,289,142 | A * | 9/1981 | Kearns | 600/529 |
| 4,473,078 | A | 9/1984 | Angel | |
| 5,386,833 | A | 2/1995 | Uhen | |
| 6,137,333 | A * | 10/2000 | Williams et al. | 327/261 |
| 6,297,661 | B1 | 10/2001 | Chen | |
| 6,405,228 | B1 * | 6/2002 | Williams et al. | 708/300 |
| 2007/0192046 | A1 * | 8/2007 | Hairston | 702/45 |

FOREIGN PATENT DOCUMENTS

| | | |
|---|---|---|
| CN | 1206337 A | 1/1990 |
| CN | 2129581 Y | 4/1993 |
| CN | 1475811 | 2/2004 |
| CN | 1559344 A | 1/2005 |
| JP | 04017836 A | 1/1992 |
| JP | A-2002-35950 | 2/2002 |
| JP | A-2004-117260 | 4/2004 |

* cited by examiner

*Primary Examiner*—Patricia C Mallari
(74) *Attorney, Agent, or Firm*—Kory D. Christensen; Stoel Rives LLP

(57) ABSTRACT

A circuit for measuring respiratory waveform with impedance method and a method and device for resisting electrical fast transient interference are provided, and wherein an output from the peak detector circuit and a reference signal are input to two input terminals of the comparator circuit, an output terminal of the comparator circuit is connected to a control terminal of the electronic switch, and one terminal of the electronic switch is connected to an output terminal of the signal amplifier circuit and the other to an input terminal of the demodulator/amplifier circuit. If a level of the output signal of the peak detector circuit is greater than the level of the reference signal, the electronic switch is switched off in response to an inversion of the output of the comparator circuit so that the interference is isolated from the next stage circuit. The present invention is prone to be implemented with significant effect.

7 Claims, 5 Drawing Sheets

CIRCUIT FOR MEASURING BREATH WAVEFORM WITH IMPEDANCE METHOD AND METHOD AND DEVICE FOR RESISTING INTERFERENCE OF ELECTRICAL FAST TRANSIENT

This application claims the benefit of Chinese Patent Application No. 200510035608.9, filed Jun. 29, 2005, the contents of which are incorporated herein by reference in their entirety.

TECHNICAL FIELD

The present invention relates to a method and device for processing pulse signals, especially for identifying pulse signals, in particular for suppressing or limiting noise or interference by switching on or off an electronic switch so as to eliminate interference.

BACKGROUND OF THE ART

A circuit for measuring respiratory waveform with impedance method is a small signal detection circuit, which is widely applied to patient monitor. Human thorax has certain basic impedance itself, and the impedance values may be slightly changed in a range from 0.1 ohm to several ohms under the frequency range from about 0.1 Hz to 2 Hz with the variation of thorax volume caused by respiratory exercises. In a method for measuring respiration with impedance methods, a stimulating signal, of which frequency is from 20 kHz to 100 kHz, is applied to a human body through electro cardiac leads, then said signal is modulated with the variation of thorax volume and the envelope of the modulated wave is deemed as a respiratory waveform. Such detection method by means of modulation can eliminate the influences resulting from contact impedance of electrodes, low frequency drift of circuits and low frequency noise.

The EFT interference (i.e., electrical fast transient interference) in power supply is caused by switching inductive loads in power grid. In different circumstances, the amplitude of the EFT interference may be up to 500-4000V with its rise time of nanosecond order, wherein a single pulse may typically persist for several ten nanoseconds, and there are generally several ten pulses with the persistence time ranging from nought point several milliseconds to several milliseconds per burst. EFT interfering signal tends to be overlapped with stimulating signal for respiratory detection through distributed capacitance due to the characteristic of high frequency and high voltage. The EFT interfering signal is returned to the ground via distributed capacitance, human body and electro cardiac leads so that the modulation circuit at the preceding stage of respiratory detection circuit may be directly affected.

Since the basic impedance of respiration generally ranges around 200-2000Ω and there is 100Ω of current-limiting resistance for defibrillation in some electro cardiac cables, the basic impedance may be up to around 4000Ω and the variable resistance lower to around 0.2Ω. Therefore, the amplification factor of measurement circuit is highly required, even up to several ten thousands times, and the occurrence of the slight interference at the preceding stage can bring great effect on respiratory signal. High frequency interference pulses such as EFT, etc. may interfere with the respiratory detection circuit with space coupling or inside the patient monitor, and impose a transient high voltage shock upon the circuit, instead of stable existence all the time, so that it is difficult to eliminate these pulses from respiratory detection signal by means of low-pass filtering. A fundamental solution is to switch off the current loop of interfering signal. For example, by means of adjusting the mechanical structure of the entire machine, the distributed capacitance between power supply of patient monitor and floating circuit is reduced so far as possible. In practice, the power line is set to keep a certain distance as long as possible from the electro cardiac leads so as to reduce the direct coupling, etc.

Below are two methods used for suppressing EFT interference in prior art.

I. The interference may be suppressed by increasing signal-to-noise ratio by means of raising the amplitude of stimulating signal and reducing the amplification factor of the output from the modulation circuit. The effect of such method is limited due to the following two aspects, one is that the amplitude of stimulating signal can not be increased unlimitedly because of the restrictions of power range of the amplifier circuit and safe current via human body, and the other is that the amplification factor at subsequent stage can not be lowered too much in order to ensure the detecting sensibility of respiratory waveform.

II. The performance of resisting EFT interference may be improved by increasing the degree of impedance match at the input sides of leads (such as RA, RLL) for collecting respiratory signal, because if the impedances at the input sides of the leads do not match, a common mode signal which is the EFT interfering signal coupling to the leads will be converted to a differential mode signal along with the result of the occurrence of interference. However, such method requires high precisions of elements and PCB wiring, so it is hard to obtain desired effect in practice.

Thus, from the above description, it can be concluded that the prior art is disadvantageous in limited effect of resisting EFT interference and high demand on circuit design.

CONTENTS OF THE INVENTION

In view of the drawbacks and limitations of the prior art, an object of the invention is to provide a circuit for measuring respiratory waveform with impedance method and a method and device for resisting electrical fast transient interference, which is adaptable to collecting respiratory waveform. According to the present invention, interference suppression can be implemented by detecting EFT interference pulses and then disconnecting the filter capacitor in filter/demodulator circuit and the preceding stage circuit during the persistence period of EFT interference such that the subsequent stage circuit is protected from interfering signal.

In accordance with an aspect of the present invention, a circuit for measuring respiratory waveform with impedance method is disclosed, which includes leads, a signal amplifier circuit, a demodulator/amplifier circuit, a filter/amplifier circuit and an A/D conversion circuit, wherein said circuit for measuring respiratory waveform with impedance method preferably further comprises a device for resisting electrical fast transient interference connected between the signal amplifier circuit and the filter/amplifier circuit.

In accordance with another aspect of the present invention, a device for resisting electrical fast transient interference is disclosed, wherein it preferably comprises a peak detector circuit, a comparator circuit and an electronic switch. The peak detector circuit is provided for receiving an interfering signal, an output thereof and a reference signal are input to two input terminals of the comparator circuit; and an output terminal of the comparator circuit is connected to a control terminal of the electronic switch.

In accordance with another aspect of the present invention, a method for resisting electrical fast transient interference is disclosed, wherein said method preferably comprises the steps of: inputting a interfering signal to a peak detector circuit; comparing a level of an output signal of the peak detector circuit with a level of a reference signal, wherein the level of the reference signal is set to be greater than a maximum level of a respiratory carrier signal; and determining whether an output of a comparator circuit is inverted based on the result of the comparison so as to make an electronic switch to be switched off or on.

According to the above method for resisting interference of electrical fast, if the level of the output signal of the peak detector circuit is greater than the level of the reference signal, the electronic switch is switched off in response to an inversion of the output of the comparator circuit; and if the level of the output signal of the peak detector circuit is less than the level of the reference signal, the electronic switch is switched on in response to another inversion of the output of the comparator circuit.

In contrast with prior art, the present invention is capable of suppressing interference by providing a high frequency peak detection circuit to detect interfering signal based on the different characteristics of respiratory detection signal and interfering signal and disconnecting the circuit for respiratory waveform detection during the persistence period of interfering signal such that the subsequent stage circuit is protected from interfering signal. The present invention is prone to be implemented with significant effect.

DETAILED DESCRIPTION OF THE PREFERRED EMBODIMENT

Now description will be given with details to further illustrate the present invention in conjunction with the drawings and preferred embodiments.

Figure 3:
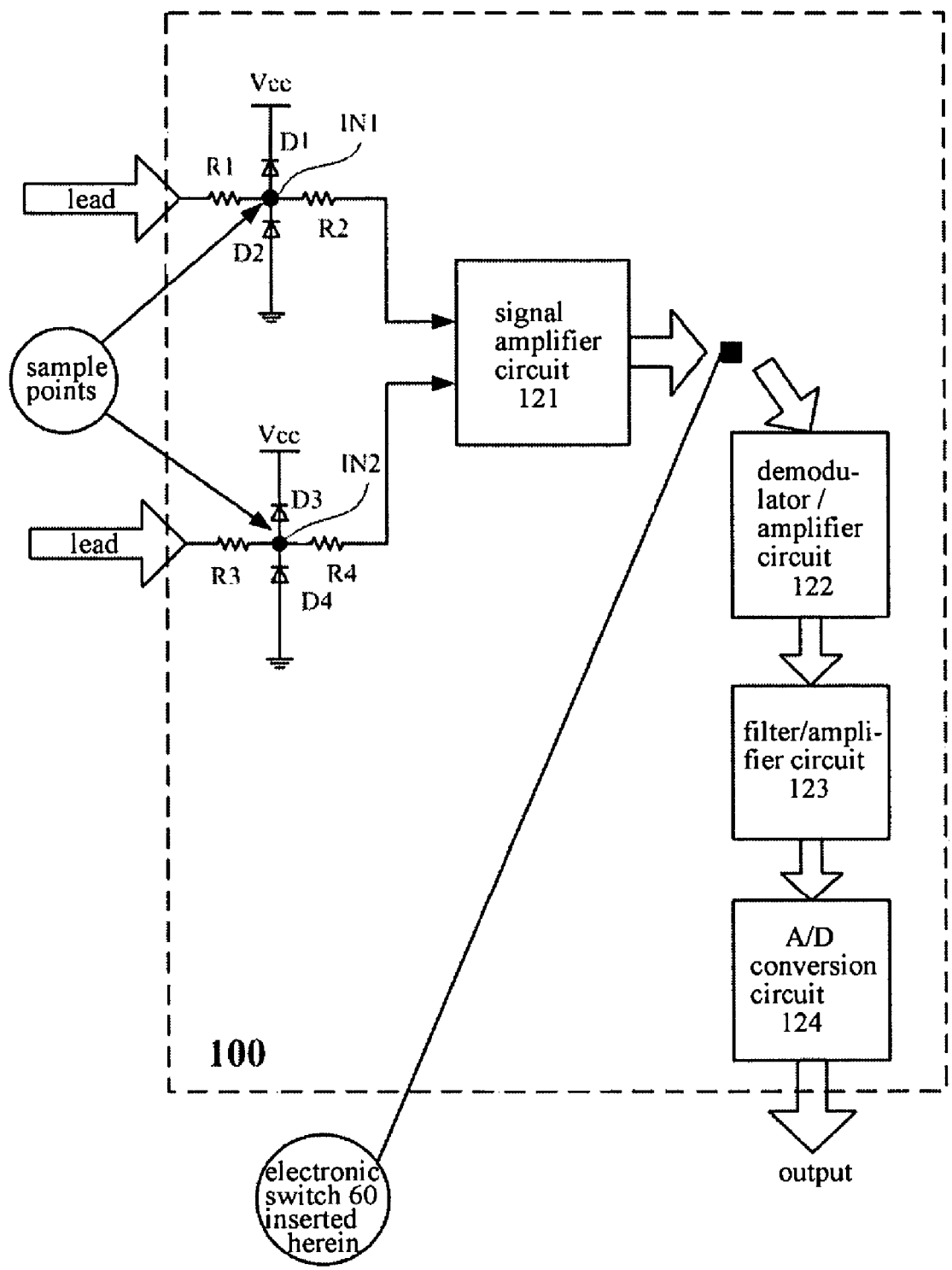
FIG. 3 is a functional block diagram showing the improvement of the circuit for measuring respiratory waveform with impedance method in prior art according to the present invention.
Figure 4:
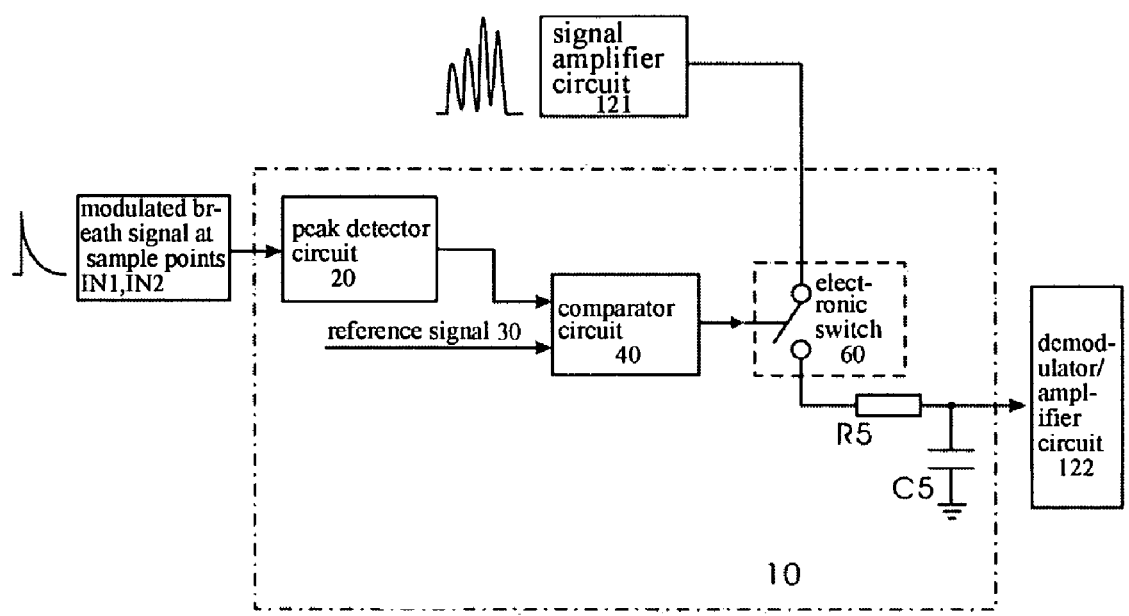
FIG. 4 is a functional block diagram showing the method and device for resisting electrical fast transient interference according to the present invention, which is adaptable to collecting respiratory waveform.

With reference to FIG. 3, a method for resisting electrical fast transient interference, which is adaptable to collecting respiratory waveform, is implemented preferably based on a circuit for measuring respiratory waveform with impedance method 100 including leads, a signal amplifier circuit 121, a demodulator/amplifier circuit 122, a filter/amplifier circuit 123 and an A/D conversion circuit 124. As shown in FIG. 4, said method comprises the steps of:

a. providing a device for resisting electrical fast transient interference 10 comprising a peak detector circuit 20, wherein not only can sample points of input signals of the peak detector circuit 20 be set on input terminals IN1 and IN2 of the signal amplifier circuit 121 respectively, but also one selected sample point to IN1 or IN2;

b. providing a reference signal 30 and a comparator circuit 40 to the device for resisting electrical fast transient interference 10, wherein an output from the peak detector circuit 20 and the reference signal 30 are input to two input terminals of the comparator circuit 40, and an output terminal of the comparator circuit 40 controls an electronic switch 60 connected between the signal amplifier circuit 121 and the demodulator/amplifier circuit 122;

c. setting a level of the reference signal 30 greater than a maximum level of a respiratory carrier signal, and setting that if the level of the output signal of the peak detector circuit 20 is greater than the level of the reference signal 30, the electronic switch 60 is switched off in response to an inversion of the output of the comparator circuit 40; and d. setting that if the interference disappears and the level of the output signal of the peak detector circuit 20 is less than the level of the reference signal 30, the electronic switch 60 is switched on in response to another inversion of the output of the comparator circuit 40 so that the signal amplifier circuit 121 and the demodulator/amplifier circuit 122 are connected.

As shown in FIG. 3, two leads may be provided to be connected to the left side and right side of the human body respectively. In the preferred embodiment, both of the two leads are used. In alternative embodiments, only one lead may be used, connected to the left side or the right side.

Figure 5:
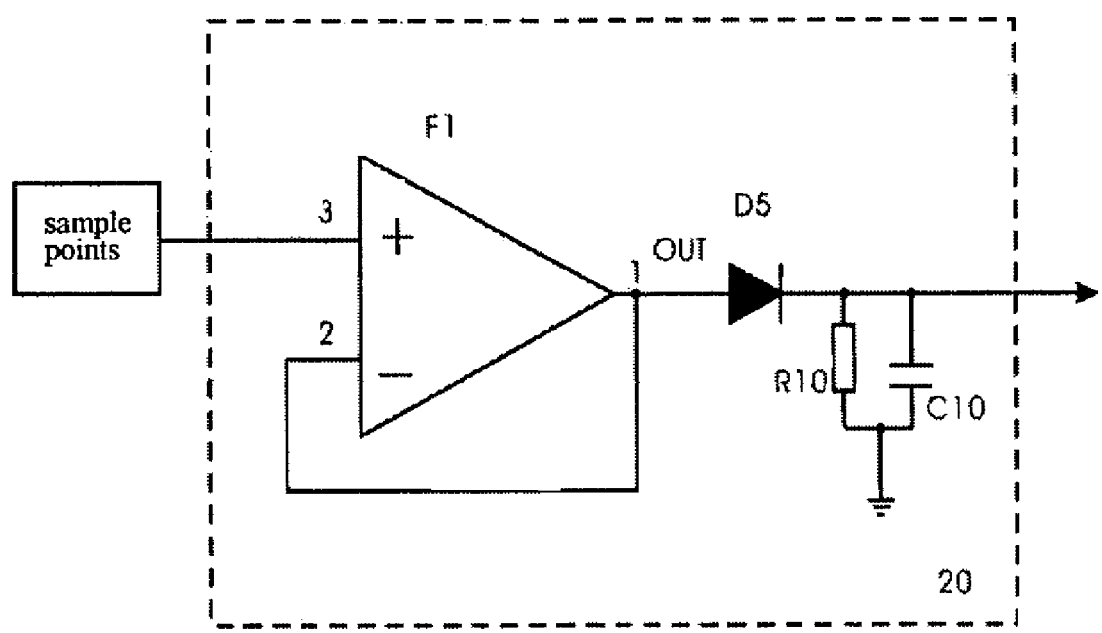
FIG. 5 is an electrical schematic diagram showing the peak detector circuit in said device according to the present invention.

As shown in FIG. 5, in the preferred embodiment, an operational amplifier F1, a diode D5, a resistor R10 and a capacitor C10 may be provided in the peak detector circuit 20. The operational amplifier F1 is provided with function as a voltage keeper, and the output terminal of which is connected to the anode of the diode D5. The resistor R10 and the capacitor C10 are connected in parallel, one terminal of which is connected to the cathode of the diode D5 and the output terminal of the entire circuit, and the other to the ground.

In the preferred embodiment, the time constant of the resistance-capacitance circuit composed of the resistor R10 and the capacitor C10 is greater than 20 ms and less than 50 ms.

The present invention may be further implemented by adopting the following technical solution.

As shown in FIGS. 3 and 4, a device for resisting electrical fast transient interference 10, which is adaptable to collecting respiratory waveform, is designed and implemented based on a circuit for measuring respiratory waveform with impedance method 100 including leads, a signal amplifier circuit 121, a demodulator/amplifier circuit 122, a filter/amplifier circuit 123 and an A/D conversion circuit 124. Particularly, said device 10 preferably comprises a peak detector circuit 20, a reference signal 30, a comparator circuit 40 and an electronic switch 60. Sample points of input signals of the peak detector circuit 20 are connected to input terminals IN1 and IN2 of the signal amplifier circuit 121. Not only can sample points in the present invention be respectively connected to input terminals IN1 and IN2 of the signal amplifier circuit 121 simultaneously, but also one selected sample point to IN1 or IN2. An output from the peak detector circuit 20 and the reference signal 30 are input to two input terminals of the comparator circuit 40, and an output terminal of the comparator circuit 40 is connected to a control terminal of the electronic switch 60. One terminal of the electronic switch 60 is connected to the output terminal of the signal amplifier circuit 121 and the other is connected to the input terminal of the demodulator/amplifier circuit 122.

The level of the reference signal 30 is set to be greater than the maximum level of the respiratory carrier signal, and if the level of the output signal of the peak detector circuit 20 is greater than the level of the reference signal 30, the electronic switch 60 is switched off in response to an inversion of the output of the comparator circuit 40. As a result, the interference is isolated.

The device for resisting electrical fast transient interference 10 also comprises a RC circuit which is a low-pass filtered circuit connected between the electronic switch 60 and the input terminal of the demodulator/amplifier circuit 122.

As shown in FIG. 5, the peak detector circuit 20 comprises an operational amplifier F1, a diode D5, a resistor R10 and a capacitor C10. The operational amplifier F1 is provided with function as a voltage keeper, and the output terminal of which is connected to the anode of the diode D5. The resistor R10 and the capacitor C10 are connected in parallel, and one terminal is connected to the cathode of the diode D5 and the output terminal of the entire circuit, and the other to the ground.

In the preferred embodiment, the time constant of the resistance-capacitance circuit composed of the resistor R10 and the capacitor C10 is greater than 20 ms and less than 50 ms. The time constant may be redetermined on other occasions.

Figure 1:
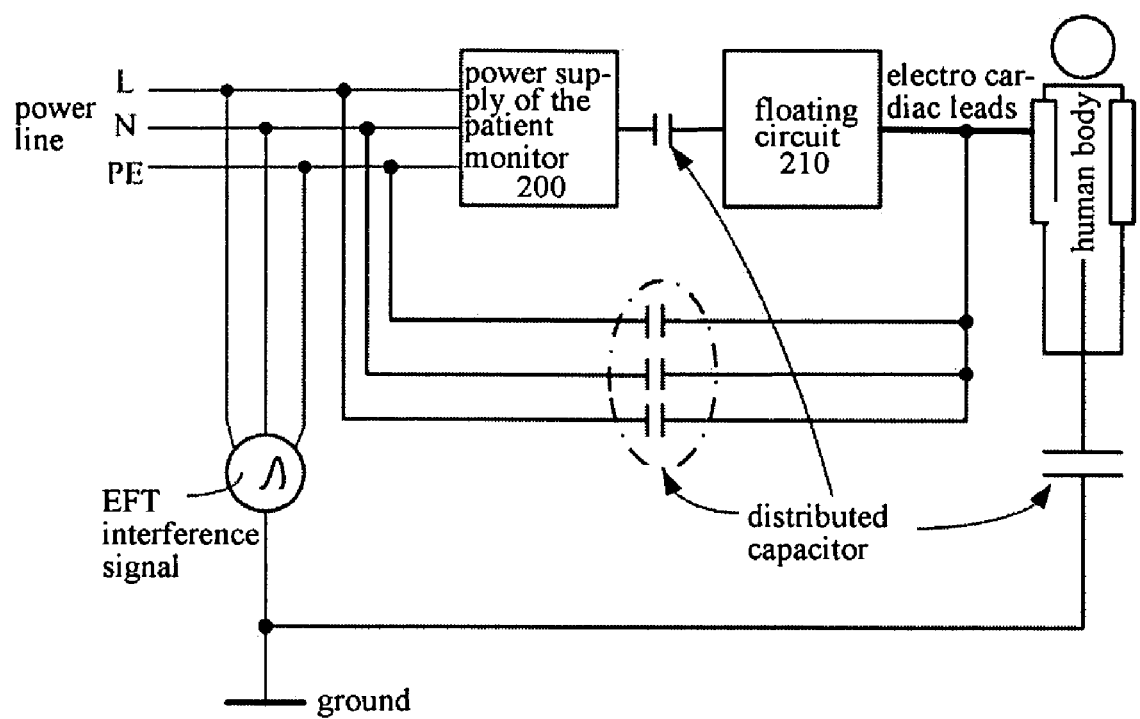
FIG. 1 is a schematic diagram illustrating the generation of electrical fast transient interference.

As shown in FIG. 1, the EFT interfering signal is returned to the ground via distributed capacitor, human body and electro cardiac leads, or returned to the ground via power supply of the patient monitor 200, distributed capacitor, floating circuit 210, electro cardiac leads, human body and distributed capacitor.

Figure 2:
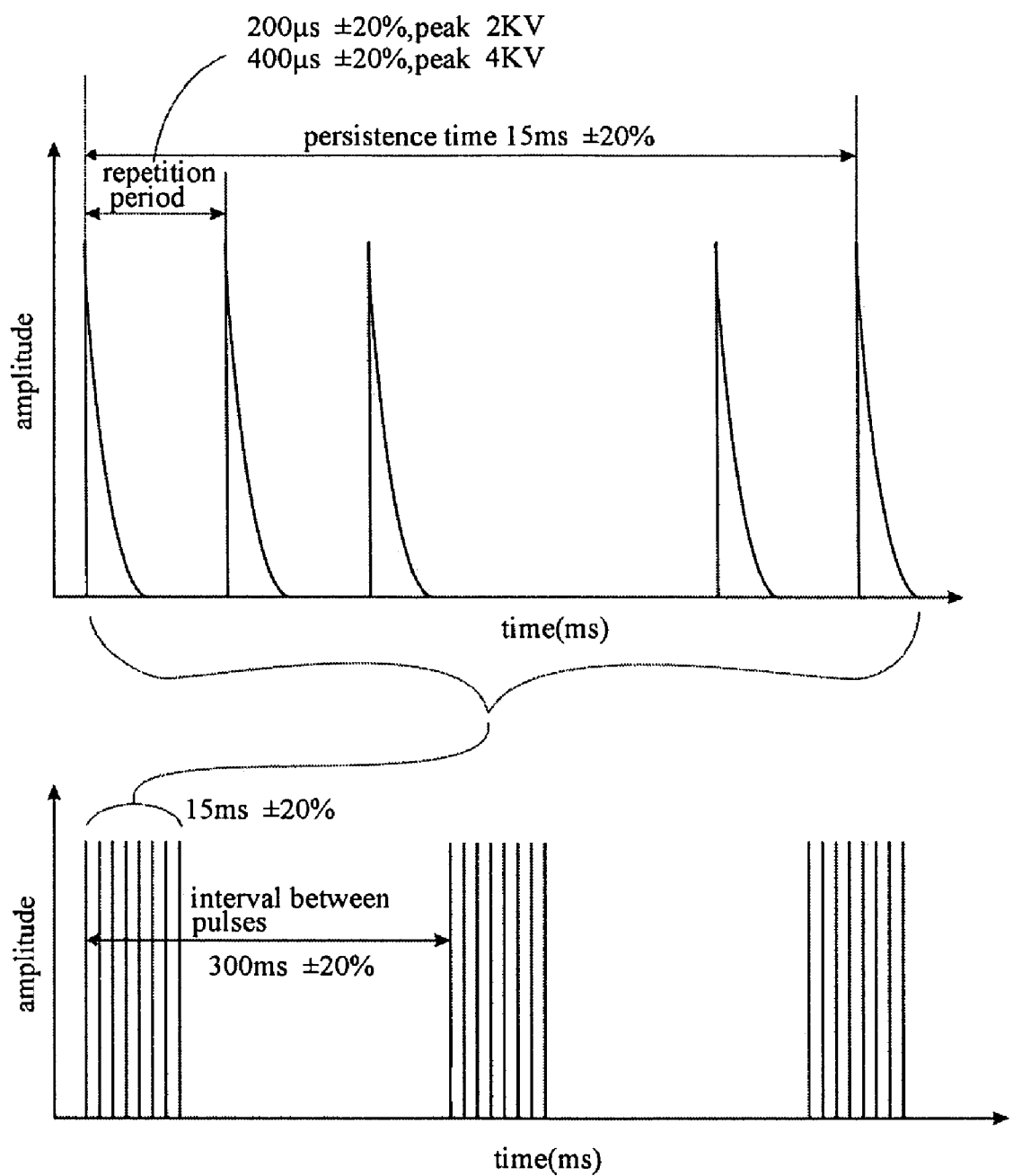
FIG. 2 is a schematic diagram illustrating quantitative analysis of electrical fast transient interference.

As shown in FIG. 2, in different circumstances, the amplitude of the EFT pulses may be up to 500-4000V with its rise time of nanosecond order, wherein a single pulse may typically persist for several ten nanoseconds, and there are generally several ten pulses with the persistence time ranging from nought point several millisecond to several milliseconds per burst.

FIG. 4 shows the principle of the device for resisting electrical fast transient interference 10. In particular, a respiratory carrier signal obtained from respiratory modulation of the stimulating signal is input to the peak detector circuit 20, and the sample peaks of interfering signal drop in the form of an exponential curve with the set time constant of the circuit. The interfering signal and the constant voltage reference signal 30 are compared, and if the level of the former is greater than that of the reference signal 30, the electronic switch 60 is switched off in response to an inversion of the output of the comparator circuit 40. As a result, the charge/discharge loop of the respiratory detector/filter circuit is switched off so that the signal of the capacitor C5 is constant. If the interfering signal is attenuated less than the reference signal 30, the electronic switch 60 is switched on again in response to another inversion of the output of the comparator circuit 40 so that the normal detection and filtering can be performed.

Since the preceding stage of the respiratory detection circuit generally adopts AC coupling to prevent the DC leakage current from exceeding threshold, the EFT interfering signal will be rectified to bidirectional pulse corresponding to rising/falling edge irrespective of the polarity of the EFT interfering signal. Therefore, the peak detector circuit 20 in FIG. 5 may also be set for unidirectional detection.

Practice proves that the present invention is capable of suppressing interference by providing a circuit for high frequency peak detection to detect interfering signal based on the different characteristics of respiratory detection signal and interfering signal and disconnecting the circuit for respiratory waveform detection during the persistence period of interfering signal such that the subsequent stage circuit is protected from interfering signal. The present invention is prone to be implemented with significant effects. In addition, the method of the present invention is adaptable to other occasions where require eliminate the random occurrence of strong interference.

What is claimed is:

1. A circuit for measuring a respiratory waveform with an impedance method, the circuit including leads, a signal amplifier circuit, a demodulator circuit, a filter circuit and an A/D conversion circuit, wherein said circuit for measuring the respiratory waveform with the impedance method further comprises a device for resisting electrical fast transient interference connected between the signal amplifier circuit and the filter circuit, and wherein the device for resisting electrical fast transient interference is configured to connect and disconnect a signal path between the signal amplifier circuit and the filter circuit based on peak levels detected on one or more signals received through the leads.

2. The circuit for measuring the respiratory waveform with the impedance method according to claim 1, wherein said device for resisting electrical fast transient interference comprises a peak detector circuit, a comparator circuit and an electronic switch, wherein sample points of input signals of the peak detector circuit are set on input terminals (IN1) and (IN2) of the signal amplifier circuit; an output from the peak detector circuit and a reference signal are input to two input terminals of the comparator circuit; an output terminal of the comparator circuit is connected to a control terminal of the electronic switch; and one terminal of the electronic switch is connected to an output terminal of the signal amplifier circuit and the other to an input terminal of the demodulator circuit.

3. The circuit for measuring the respiratory waveform with the impedance method according to claim 2, wherein a level of the reference signal is greater than a maximum level of a respiratory carrier signal and, if a level of the output signal of the peak detector circuit is greater than the level of the reference signal, the electronic switch is switched off in response to an inversion of the output of the comparator circuit.

4. The circuit for measuring the respiratory waveform with the impedance method according to claim 3, wherein said device for resisting electrical fast transient interference also comprises an RC (resistor-capacitor) circuit connected between the electronic switch and the input terminal of the demodulator circuit.

5. The circuit for measuring the respiratory waveform with the impedance method according to claim 4, wherein said peak detector circuit comprises an operational amplifier (F1), a diode (D5), a resistor (R10) and a capacitor (C1), in which the operational amplifier (F1) is provided with function as a voltage keeper, an output terminal of which is connected to an anode of the diode (D5); and the resistor (R10) and the capacitor (C10) are connected in parallel, one terminal of which is connected to a cathode of the diode (D5) and an output terminal of the peak detector circuit, and the other to the ground.

6. The circuit for measuring the respiratory waveform with the impedance method according to claim 5, wherein the time constant of the resistance-capacitance circuit composed of said resistor (R10) and capacitor (C10) is greater than 20 ms and less than 50 ms.

7. The circuit for measuring the respiratory waveform with the impedance method according to claim 6, wherein one of said sample points is connected to input terminals (IN1) or (IN2) of the signal amplifier circuit.

* * * * *